United States Patent

Matsui et al.

[11] Patent Number: 5,900,197
[45] Date of Patent: May 4, 1999

[54] PRODUCTION PROCESS OF POROUS RETAINER FOR ROLLING BEARING

[75] Inventors: Akira Matsui, 28-44, Tenjugaoka-cho, Hanazono, Ukyo-ku, Kyoto, 616; Yoshinori Morita, Shiga; Fuminori Satoji; Masayuki Yamazaki, both of Mie, all of Japan

[73] Assignees: Akira Matsui; J. Morita Manufacturing Corporation, both of Kyoto; NTN Corporation, Osaka, all of Japan

[21] Appl. No.: 08/940,428

[22] Filed: Sep. 30, 1997

[30] Foreign Application Priority Data

Oct. 1, 1996 [JP] Japan ............................. 8-278548

[51] Int. Cl.[6] ............................................. B29C 67/20
[52] U.S. Cl. ................................... 264/49; 264/344
[58] Field of Search ................................ 264/49, 344

[56] References Cited

U.S. PATENT DOCUMENTS

| | | | |
|---|---|---|---|
| 3,917,761 | 11/1975 | Scheuerlein et al. | 264/49 |
| 4,020,230 | 4/1977 | Mahoney et al. | 264/49 |
| 4,099,218 | 7/1978 | Klein et al. | 264/49 |
| 4,115,492 | 9/1978 | Mahoney et al. | 264/49 |
| 4,963,304 | 10/1990 | Im et al. | 264/49 |
| 5,091,087 | 2/1992 | Calundann et al. | 264/49 |

*Primary Examiner*—Allan R. Kuhns
*Attorney, Agent, or Firm*—Koda & Androlia

[57] ABSTRACT

A process is provided for the production of a porous retainer for use in a rolling bearing for holding rolling elements. The process comprises the following steps:

(1) blending a polyimide resin, which serves as a porous matrix material for the porous retainer, with another heat-resistant resin which has a forming temperature range close to the polyimide resin and, when treated with a solvent in the presence of the polyimide resin, is solely dissolved out;

(2) forming the resulting resin blend into a retainer of a desired shape; and (3) treating the thus-formed retainer with the solvent, whereby the another heat-resistant resin is solely dissolved out.

5 Claims, 2 Drawing Sheets

PRODUCTION PROCESS OF POROUS RETAINER FOR ROLLING BEARING

BACKGROUND OF THE INVENTION a) Field of the Invention

This invention relates to a production process of a rolling bearing for a high-speed rotating equipment employed in a field where high speed and high safety are required, such as a medical, food-processing or aerospace equipment.

More specifically, the present invention is concerned with an efficient and economical production process of a porous retainer of the type that as a principal element of a rolling bearing, it is used in a form impregnated with a lubricating oil.

b) Description of the Related Art

Conventional examples of a retainer for holding rolling elements (balls) in a rolling bearing include those made of a self-lubricating molding material, for example, a synthetic resin such as polytetrafluoroethylene.

Further, as examples of an inner ring, an outer ring, rolling elements and a retainer in a bearing, there are those obtained by plating, coating or sputtering these members with a solid lubricant, for example, a metal such as gold or silver, or molybdenum disulfide.

It is however the current situation that a bearing element, for example, a retainer making use of the above-described self-lubricating synthetic resin or the above-described solid lubricant such as gold or silver is generally poor in the durability of a lubricant film and cannot stably exhibit sliding properties over a long time.

Especially in a lubrication system of a high-speed rotating equipment such as a high-speed cutter, it is strongly required to stably and continuously supply a lubricating oil onto a friction surface in a bearing for many hours and also to provide the friction surface with wear resistance. To the best of the inventors' knowledge, there is no retainer which can meet such needs.

A high-speed rotating equipment, especially a high-speed cutter for rotating a cutting tool at high speeds is generally constructed of a rotary shaft for fixedly holding various cutting tools thereon, a drive unit for rotating the rotary shaft, and a bearing unit rotatably supporting the rotary shaft.

As a high-speed cutter of this type, an odonto-therapeutic high-speed cutter (i.e., air turbine hand piece) can be mentioned by way of example.

Bearing units for the above-mentioned odonto-therapeutic high-speed cutters (i.e., air turbine hand pieces) are known to include those having a ball bearing system making use o f balls (rolling elements) and those equipped with a (non-contact) air bearing system making use of an air bearing.

Paying attention, for example, to the bearing mechanisms of dental air turbine hand pieces, two types of air turbine hand pieces are known, one being of the ball bearing turbine type and the other of the air bearing turbine type.

The former type, i.e., the ball bearing turbine type can be considered to be a high-speed rotation type for approximately 200,000 to 400,000 rpm, while the latter type, that is, the ball bearing turbine type can be considered to be a super high-speed rotation type for approximately 300,000 to 500,000 rpm.

It is however to be noted that the above-described revolution speeds of the ball bearing turbine type and the air bearing turbine type are general values. For example, the dental air turbine hand piece already proposed by the present inventors (U.S. Pat. No. 5,562,446) is of the ball bearing turbine type. Nonetheless, it has high performance so that super high-speed rotation can be achieved.

To facilitate the understanding of the conventional art and this invention, a description will now be made about the construction of an equipment to which a bearing making use of a porous retainer produced by the production process of this invention and a lubricating oil, is applied, namely, of a dental high-speed cutter (i.e., a dental air turbine hand piece).

FIG. 1 to FIG. 2 show the construction of the dental air turbine hand piece, in which FIG. 1 is a perspective view illustrating the overall construction and FIG. 2 is a cross-sectional view illustrating the internal construction of a head portion and a neck portion in particular.

As is depicted in FIG. 1, the dental air turbine hand piece designated generally by letter A is composed of a head portion H, which carries a cutting tool B(5) fixedly held on a rotor shaft (drive shaft) of an air turbine, and a grip portion G.

A neck portion N of the grip portion G is connected to the head H, and is internally provided with means for supplying compressed air to the air turbine arranged within the head portion H and also for discharging compressed air from the air turbine.

FIG. 2 illustrates the internal construction of the head portion H and the neck portion N of the dental air turbine hand piece A.

As is illustrated in the figure, in the head portion H, a turbine rotor shaft 3 with turbine blades 2 disposed at a peripheral edge portion thereof is arranged within a chamber 11 of a head 1, and the turbine rotor shaft 3 is rotatably supported within the head 1 by way of a bearing unit 4.

The head 1 is composed of a head main part 12 and a cap part 13. Within the head main part 12, the bearing unit 4 is arranged to rotatably support the turbine rotor shaft 3. To perform treatment, the cutting tool 5 is fixedly held in a bore which is formed through the turbine rotor shaft 3 along a central axis thereof. Incidentally, the cutting tool 5 is provided on a peripheral side wall thereof with a chuck 51 for holding the cutting tool 5 in place within the bore.

The bearing unit 4 is of the ball bearing type and is constructed of an inner ring 41, an outer ring 42, rolling elements 43 and a retainer 44. The bearing unit 4 may be provided on an outer periphery or side wall thereof with O-rings for providing the bearing unit with self-centering function and/or with known wave washers for enhancing the rigidity of the shaft.

A main part 6 of the neck portion N is provided with an air supply passage 7 and an air inlet 71 for supplying compressed air t o the turbine blades 2 arranged within the chamber 11 and also with air discharge passages 8,9 and air outlets 81,91 for discharging compressed air from the chamber 11.

In the above-described internal construction of the dental air turbine hand piece A as illustrated in FIG. 2, the means for supplying and discharging compressed air is the one already proposed by the present inventors (U.S. Pat. No. 5,562,446) and is of a new construction totally unseen in the conventional art.

Accordingly, FIG. 2 contains other reference symbols in addition to those referred to in the above to describe the individual elements (members). Although a description of these additional symbols is omitted herein, the construction of the conventional dental air turbine hand piece can be easily understood on the basis of FIG. 2.

The dental air turbine hand piece A—which is equipped with the air supply and discharge means shown in FIG. 2 and already proposed by the present inventors—belongs to the category of conventional hand pieces with a rolling bearing built therein, but makes it possible to obtain rotation of an extremely high speed and hence a large torque.

In the above-described dental air turbine hand piece of the ball bearing type, its bearing unit is in the form of a miniature bearing unit. Since the turbine rotor shaft rotates at a high speed of approximately 200,000 to 400,000 revolutions per minute, the temperature inside the bearing unit becomes high and further, the bearing unit is exposed to a large stress. For a lubricating oil to be applied to a bearing which is used under the above-described severe conditions, it is therefore extremely important to control its quality and properties.

Further, the above-described dental air turbine hand piece of the ball bearing type is used in the oral cavity. Accordingly, the dental air turbine hand piece is used by spraying or dropping a lubricating oil to the bearing unit, in other words, is used under an environment of minimum lubrication, and is subjected to high-pressure and high-temperature treatment for sterilization and disinfection (which is also called "autoclaving", which is applied under the following conditions: steam pressure, 2.4 kg/cm$^2$; temperature, 135° C.; time, 5 minutes).

As a rolling bearing for use in the above-described dental air turbine hand piece, one capable of meeting conditions similar to those mentioned above is therefore required. In particular, as a retainer which acts as an important element in a lubrication system, one capable of satisfying conditions similar to those mentioned above is required.

Further, without needing mentioning, the lubricating oil for use in the above bearing is also required to have properties sufficient to withstand such severe use conditions, such as oxidation resistance.

Conventional examples of the above-described retainer for rolling elements (balls) include those made of polyimide resins or fiber-layer-containing phenol resins from the viewpoint of the above-described property requirements. These conventional retainers are however not considered to be sufficient.

In view of the above-described severe use conditions for dental air turbine hand pieces, dental air turbine hand pieces equipped with retainers impregnated with fluorinated oils, which have excellent heat resistance, permit sterilization and disinfection (autoclaving) and have superb lubricity, have been proposed recently in Japanese Patent Publication (Kokoku) No. HEI 5-43884 and Japanese Utility Model Application Laid-Open (Kokai) No. HEI 7-10553.

Incidentally, the retainers are in the form of porous members obtained by sintering powder of a polyimide resin.

The fluorinated oils have properties such that they are inactive, are excellent in heat resistance, chemical resistance and solvent resistance and, even when exposed to high temperatures, do not form a solid deterioration material. It is therefore possible to consider that the above-described proposed dental air turbine hand pieces have used these properties for the retainers.

Concerning a rolling bearing for a high-speed rotating equipment, for example, for a dental air turbine hand piece of the ball bearing type, especially a retainer as a principal element of the rolling bearing, a variety of examples of different materials and structures have been developed in the light of required characteristics as described above.

For example, as a rolling bearing for a dental air turbine hand piece of the high-speed rotation system, especially as its retainer, a porous product obtained by sintering powder of a polyimide resin from the viewpoint of heat resistance (autoclaving resistance), durability and the like as mentioned above has been proposed.

As the above-mentioned porous retainer made of the polyimide resin is produced by compressing and sintering powder of a polyimide resin of a desired particle size (for example, 15 to 50 μm) under desired conditions, it is however difficult to form a porous portion of a uniform communicated structure in the matrix material.

Needless to say, a failure in forming a porous portion of a uniform communicated structure in a matrix material (polyimide resin) means that the matrix material cannot be impregnated evenly with a lubricating oil. This uneven impregnation will then give serious adverse effects on lubrication characteristics in a high-speed rotation system.

In the production of a porous retainer by the above-described sintering of power of a polyimide resin, it is extremely difficult especially in providing the porous retainer with uniform quality. The production must therefore be performed under stringent conditions.

SUMMARY OF THE INVENTION

The present invention has been completed in view of the above-described problems of the bearings in the conventional high-speed rotating equipments such as dental air turbine hand pieces.

Incidentally, the direct motive for the present invention resided in the lack of a lubricating oil of excellent properties for the high-performance and high-speed rotating, dental air turbine hand piece of the ball bearing turbine type previously proposed by the present inventors (U.S. Pat. No. 5,562,446).

An object of this invention is to provide a novel production process which can replace especially the above-described production method of a porous polyimide resin retainer by sintering, namely, to provide a novel production process of a porous retainer made of a polyimide resin, said process assuring uniform quality and being excellent in economy.

With a view to developing a novel production process of a porous retainer from a polyimide resin as a base resin, the present inventors have proceeded with an extensive investigation. As a result, it has been found that porous retainers applicable to high-speed rotating systems can be stably and economically produced from a combination of a polyimide resin, which can serve as a porous matrix material, and another heat-resistant resin which has substantially the same forming temperature range as the polyimide resin and can be solely dissolved out with a solvent subsequent to its forming as a polymer blend with the polyimide resin.

The present invention has been completed based on the above-described finding and provides a porous retainer of high quality and excellent economy for a rolling bearing in a high-speed rotating equipment such as a dental air turbine hand piece.

Describing the present invention in brief, the present invention provides a process for the production of a porous retainer for use in a rolling bearing for holding rolling elements (balls), which comprises the following steps:

(1) blending a polyimide resin, which serves as a porous matrix material for the porous retainer, with another heat-resistant resin which has a forming temperature range close to the polyimide resin and, when treated with a solvent in the presence of the polyimide resin, is solely dissolved out;

(2) forming the resulting resin blend into a retainer of a desired shape; and (3) treating the thus-formed retainer with the solvent, whereby the another heat-resistant resin is solely dissolved out.

The polyimide retainer (which may hereinafter be referred to as the "dissolved-out polyimide retainer") produced by the production process of this invention making use of the solvent dissolution technique has far superior characteristics to conventional non-porous polyimide retainers and, even when compared with porous polyimide retainers by conventional sintering processes (which may hereinafter be referred to as "sintered porous polyimide retainers"), exhibits superb characteristics.

Further, the production process of this invention making use of the solvent dissolution technique has advantages that, compared with the conventional sintering processes, it can be practiced more simply and easily and retainers of high-quality can be economically produced in a large quantity.

It should be noted that the term "polyimide" as used herein shall embrace not only polyimide resins (PI) but also polyamideimide resins (PAI).

DETAILED DESCRIPTION OF THE INVENTION AND PREFERRED EMBODIMENTS

Figure 1:
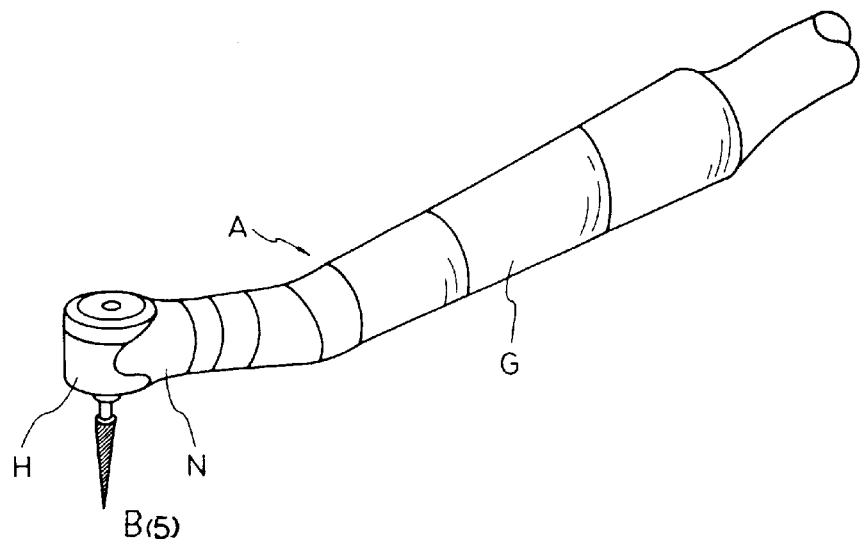
FIG. 1 is a perspective view of a dental air turbine hand piece equipped with a porous retainer of the lubricating-oil-impregnated type produced by the process of the present invention.

The technical constitution and embodiments of the present invention will hereinafter be described in detail.

In the production process of this invention for the porous retainer, a polyimide resin which should become a porous matrix material is chosen out of heat-resistant resins from the viewpoint that the porous retainer is applied to a high-speed rotation system and is supposed to exhibit high performance.

In the present invention, the above-mentioned polyimide resin (hereinafter abbreviated as "the PI resin") is a resin obtained by subjecting an aromatic carboxylic acid and an aromatic amine to condensation polymerization and containing imide bonds in the backbone thereof (which may be either thermoplastic or thermosetting), and is excellent in heat resistance, chemical resistance, mechanical properties and electrical characteristics.

In the present invention, the term "PI resin" should be interpreted to also include polyamideimide resins (hereinafter abbreviated as "the PAI resins") containing imide bonds and amide bonds in their backbones as mentioned above.

In the present invention, a commercially-available PI resin or PAI resin can be conveniently used as the PI resin or PAI resin for molding the porous retainer. As commercially-available PI resins and PAI resins, the following resins can be exemplified including their chemical structural formulas.

(i) PI resins:
  (1) "P94-HT" [trade name; product of Lenzing AG, Austria; represented by the below-described chemical formula (1) in which R represents an alkylene group];
  (2) "TI-3000" [trade name; product of Toray Industries, Inc.; represented by the below-described chemical formula (2)];
  (3) "UIP-S" [trade name; product of Ube Industries, Ltd.; represented by the below-described chemical formula (3)];
  (4) "Vespel" [trade name; product of E.I. du Pont de Nemours & Co., Ltd.; represented by the below-described chemical formula (2)];
  (5) "Aurum" [trade name; product of Mitsui-Toatsu Chemicals Inc.; represented by the below-described chemical formula (4)]; and
  (6) Others, including "Meldin 8100" and "Meldin 900", products of Furon, U.S.A.

(ii) PAI resins:
  (1) "Torlon 4000 TF" [trade name; product of Amoco Chemical Corp.; represented by the below-described chemical formula (5) in which Ph represents a phenylene group].

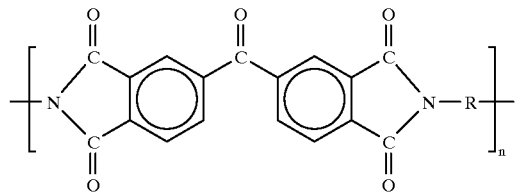

Chemical formula (1)

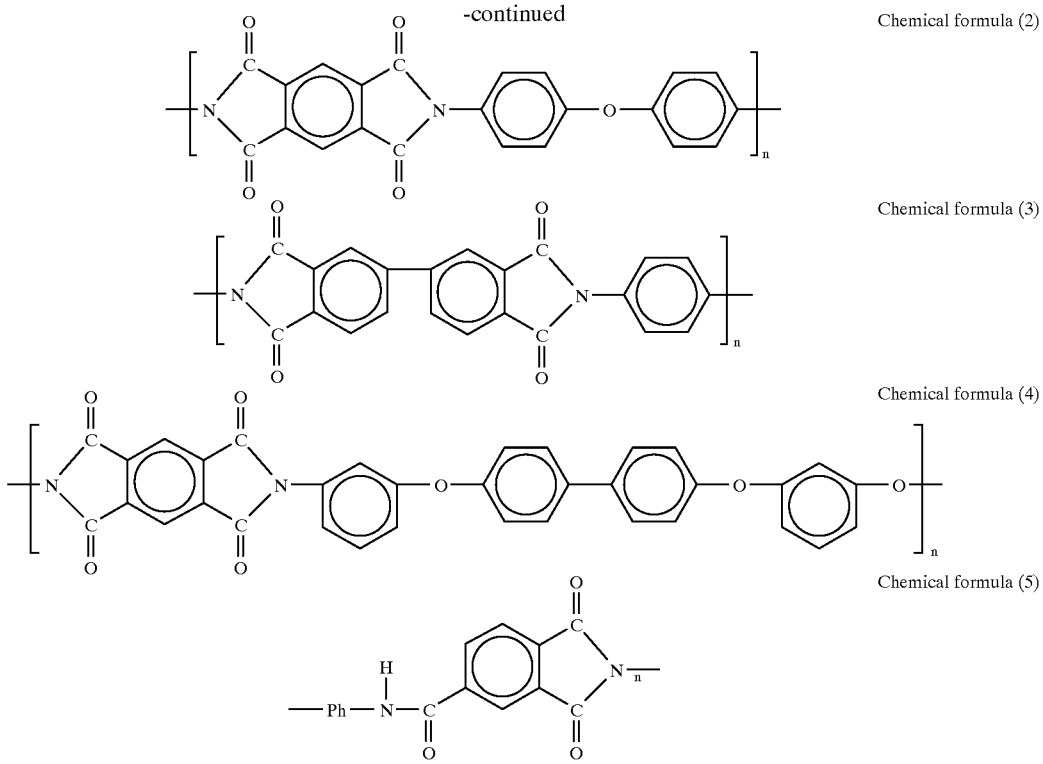

Chemical formula (2)

Chemical formula (3)

Chemical formula (4)

Chemical formula (5)

In the present invention, the another heat-resistant resin combined with the polyimide resin (incidentally, this term should be interpreted in a broad sense so that it also embraces polyamideimide resins as pointed out above), which becomes the porous matrix material, can be chosen as desired.

The forming temperature range of the polyimide resin which serves as the porous matrix material, for example, the temperature range for its injection molding is 400 to 420° C. for thermoplastic polyimides (TPIs) and 340–350° C. for polyamideimides (PAIs). As the another heat-resistant resin, one having a forming temperature range close to the above-described forming temperature range is therefore chosen.

In the present invention, the forming method is not limited to the above-mentioned injection molding. Besides, a desired forming method such as melt forming, compression molding or extrusion can be adopted. The another heat-resistant resin should be chosen in relation to its forming method.

Needless to say, the another heat-resistant resins should also be chosen depending on the kind of the solvent employed in the step (3), namely, in the solvent dissolution step.

When methylene chloride (dichloromethane) is adopted by way of example in the step (3), the following resins can be used as the another heat-resistant resin. For the sake of reference, each resin will be followed by its injection molding temperature (° C.).

(i) Polyether imides (PEIs) (340–425° C.)
(ii) Polyether sulfones (PESS) (350–370° C.)
(iii) Polysulfones (PSFs) (330–400° C.)
(iv) Polyarylates (PARs) (340–360° C.)

In the present invention, usable examples of the solvent in the step (3) can include, in addition to the above-mentioned methylene chloride (dichloromethane), chloroform, methyl ethyl ketone (MEK), tetrahydrofuran (THF), N-methylpyrrolidone (NMP), and N,N-dimethylformamide (DMF).

When the polyimide resin which becomes the porous matrix material is used in the form of powder in the present invention, powder is used after classified and sifted generally to an average particle size of from 15 to 50 $\mu$m. On the other hand, the another heat-resistant resin generally has an average particle size similar to that of the polyimide resin, although not necessarily limited to such an average particle size. Needless to say, the average particles sizes of both the resins can be set as desired in view of the pore size of a communicated structured intended to be formed.

When the PI or PAI resin which becomes the porous matrix material is used in the form of powder in the present invention, the ratio of the resin powder to the powder of the another heat-resistant resin can be set as desired in view of a porosity (by volume), the size and density of pores in the communicated structure, etc.

In general, the former powder, i.e., the PI or PAI resin powder can be used in a proportion of from 50 to 95 parts by weight while the latter powder, i.e., the powder of the another heat-resistant resin can be used in a proportion of from 5 to 50 parts by weight.

In the present invention, the step (2), namely, the step in which the blend of the PI or PAI resin, which will become the porous matrix material, with the another heat-resistant resin is formed into the retainer of the desired shape can be performed under desired forming conditions.

Without needing mentioning, as the forming conditions for the step (2), it is preferred to use conditions such that particle boundaries of both the components are maintained in a molten state to achieve fusion bonding therebetween. As a forming method, melt forming, compression molding, extrusion or injection molding can be adopted as described above.

When the porous matrix material is formed of a PAI resin, the forming conditions for the step (2) can be determined with reference to the conditions for the production of a molded porous body from powder of the PAI resin by sintering.

In the case of compression molding of a PAI resin, for example, the following molding conditions can be adopted: molding pressure, 2,500–3,000 kg/cm$^2$; heating temperature, 300° C.

In the case of compression molding of a PI resin, on the other hand, the following molding conditions can be adopted: molding pressure, 5,000 kg/cm$^2$; heating temperature, 400° C.

When a PAI resin or PI resin is subjected to injection molding in the present invention, conditions for the injection molding can be set as desired. In this case, for example, another heat-resistant resin such as a polyether imide (PEI) can be blended with the PAI resin or PI resin. Subsequent to thorough mixing in a Henschel mixer, the resulting resin blend can be pelletized through a twin-screw melt extruder. The pellets can then be injection-molded into a desired mold by an injection molding machine, thereby molding a retainer.

To produce a porous retainer from the non-porous retainer produced as described above, it is only necessary to immerse the non-porous retainer in a methylene chloride solution and then to apply ultrasonic waves thereto on an ultrasonic washer. In this manner, the another heat-resistant resin such as the PEI resin is dissolved out, thereby resulting in the formation of a porous retainer. The following washing conditions can be adopted for the ultrasonic washer: temperature, 25° C.; time, 30 minutes.

When a PAI resin or PI resin is subjected to extrusion in the present invention, the extrusion can be performed in a similar manner as the above-described injection molding except for the use of an extruder.

In the present invention, the step (3), that is, the step in which the another heat-resistant resin component is dissolved out with the solvent from the formed body (the non-porous retainer of the desired shape) obtained in the step (2) can be performed under desired conditions.

For example, when methylene chloride (dichloroethane) is used as the solvent, the step (3) can be performed by immersing the non-porous retainer in a beaker with methylene chloride placed therein and then applying ultrasonic waves on an ultrasonic washer (25° C., 30 min).

According to the production process of the present invention which comprises the above-described steps (1) to (3), a porous retainer having a desired porosity (for example, 0.5 to 20% by volume) and a porous portion of a uniform communicated structure can be produced efficiently and economically.

A description will next be made about the lubricating oil with which the porous retainer produced by the above-described production process of this invention is impregnated.

The porous retainer obtained by the above-described production process of this invention can be used by impregnating it with a conventionally-known lubricating oil, to say nothing of a nondrying vegetable oil which has been found to be useful especially as a lubricating oil for a high-speed rotation system by the present inventors.

Needless to say, for making improvements in lubrication characteristics, characteristics of an applied lubricating oil itself are also important in addition to the constitution and structure of a retainer.

Hereinafter, a description will first be made about nondrying vegetable oils which have been found for the first time by the present inventors to be useful as lubricating oils for rolling bearings in high-speed rotating equipments, followed by a description of other impregnating oils.

Roughly dividing, vegetable oils can be classified into the following three types:

(i) Nondrying oils:

The term "nondrying oil" means an oil which does not form any film-like matter (resinous solid) even when dried (oxidized) in the form of a thin layer in air.

A nondrying oil of this type contains unsaturated fatty acids, each of which contains two or more double bonds per molecule (hereinafter called "poly-unsaturated fatty acids), only in small amounts and is primarily composed of the glyceride (glycerol ester) of oleic acid (which contains one double bond per molecule), and its iodine value (a scale indicating the degree of unsaturation of an oil) is 100 or smaller.

Representative examples of nondrying oils of this type can include olive oil, arachis oil and oleysol oil.

(ii) Semidrying oils:

The term "semidrying oil" means an oil which shows intermediate properties between a nondrying oil and a drying oil to be described next. Its iodine value is from 100 to 130.

Representative examples of semidrying oils of this type can include rapeseed oil, sesame oil and cotton seed oil.

(iii) Drying oils:

The term "drying oil" means an oil which forms a film (resinous solid) when dried (oxidized) in the form of a thin layer in air. A drying oil of this type is composed of glycerides of fatty acids having high degrees of unsaturation (for example, linoleic acid contains two double bonds and linolenic contains three double bonds). These glycerides absorb oxygen in air and undergo oxidative polymerization, whereby a film-like matter is easily formed. Incidentally, the iodine value of such a drying oil is 130 or greater.

Typical examples of drying oils of this type can include linseed oil and tung oil.

Among the above-described various vegetable oils, nondrying oils are oils and fats (glycerol esters of fatty acids) each of which does not form a film-like matter (resinous solid) even when dried (oxidized) in the form of a thin layer. As they are excellent in heat resistance (so that sterilization and disinfection by autoclaving is feasible) and durability, they are suitable as lubricating oils for rolling bearings in high-speed rotating equipments such as dental air turbine hand pieces.

In a rolling bearing of a high-speed rotating equipment, such as a dental air turbine hand piece, in which a porous retainer produced in accordance with the present invention is assembled, the above-described nondrying vegetable oil is extremely useful as a lubricating oil.

A description will hereinafter be made in detail about olive oil, a representative example of the above-described nondrying vegetable oils.

Olive oil is an oil (glycerol esters) available from drupes of *Olea Europaea*. Roughly driving, its components can be classified into the following three types:

(i) unsaturated resin acids;

(ii) saturated resin acids; and (iii) various trace components.

The unsaturated resin acids in olive oil are generally composed of mono-unsaturated and di- and higher-unsaturated (poly-unsaturated) resin acids.

The kinds and contents of the unsaturated resin acids in olive oil will be shown below:

1) Oleic acid (mono-unsaturated) . . . 56.0–83.0%

$CH_3(CH_2)_7CH=CH(CH_2)_7COOH$

2) Linoleic acid (poly-unsaturated) . . . 3.5–20.0%

$CH_3(CH_2)_4CH=CHCH_2CH=CH(CH_2)_7COOH$

3) Palmitoleic acid (mono-unsaturated) . . . 0.3–3.5%

$CH_3(CH_2)_5CH=CH(CH_2)_7COOH$

4) Linolenic acid (poly-unsaturated) . . . 0.0–1.5%

$CH_3CH_2CH=CHCH_2CH=CHCH_2CH=CH(CH_2)_7COOH$

5) Gadoleic acid (mono-unsaturated) . . . 0.0–0.05%

$CH_3(CH_2)_9CH=CH(CH_2)_7COOH$

As has been described above, olive oil abundantly contains oleic acid which is a mono-unsaturated fatty acid. Olive oil also contains poly-unsaturated fatty acids, such as linoleic acid, in small amounts.

As has also been described above, a poly-unsaturated fatty acid is susceptible to oxidation. Nonetheless, olive oil has excellent oxidation resistance as a whole because, as will be described subsequently herein, olive oil contains tocopherols (vitamin E) as trace components and poly-unsaturated fatty acids such as linolenic acid are protected from oxidative deterioration owing to the anti-oxidation action of the tocopherols (vitamin E).

A description will next be made about saturated fatty acid components in olive oil.

The kinds and contents of saturated fatty acids in olive oil will be shown below:

1) Palmitic acid $CH_3(CH_2)_{14}COOH$ . . . 7.5–20.0%
2) Stearic acid $CH_3(CH_2)_{16}COOH$ . . . 0.5–3.5%
3) Myristic acid $CH_3(CH_2)_{12}COOH$ . . . 0.0–0.05%
4) Arachidic acid $CH_3(CH_2)_{18}COOH$ . . . 0.0–0.05%
5) Behenic acid $CH_3(CH_2)_{20}COOH$ . . . 0.0–0.05%
6) Lignoceric acid $CH_3(CH_2)_{22}COOH$ . . . 0.0–0.05%

As is appreciated from the foregoing, olive oil can be considered to have low contents of saturated fatty acids which cause hypercholesterolemia.

Next, a description will be made of various trace components in olive oil.

The kinds of various trace components in olive oil will hereinafter be described along with their properties and functions.

(1) Unsaponifiable materials:
(a) Sterols
(b) Hydrocarbons
  Squalene
  Aromatic hydrocarbons (which impart inherent sensory characteristics, namely, aroma and flavor)
(c) Tocopherols (oxidation-preventing function)
  α-tocopherol (vitamin E) (prevention of blackening and polymerization)
  β, γ, δ-tocopherols (prevention of rancidity which would otherwise be caused by the existence of one or more heavy metals)
(d) Triterpene alcohols
  Cycloalterenol
  Erythrodiol
(e) Fat-soluble vitamins
  Vitamins A, D (anti-oxidation effects)
(2) Phospholipids, chlorophyll and derivatives:
(a) Phospholipids
(b) Chlorophyll (anti-oxidation effect)
(3) Phenolic compounds:
(a) Phenolic compounds (anti-oxidation effects)
(b) Polyphenols (anti-oxidation effects)

As is appreciated from the foregoing, olive oil has higher contents of various trace components, which act against oxidation of oils and fats, than other non-drying oils and drying oils, and can therefore provide a lubricating oil excellent in heat resistance (so that sterilization and disinfection by autoclaving is feasible) and durability.

A description will next be made about other non-drying vegetable oils which are useful as lubricating oils for a bearing in a high-speed rotating equipment, such as a dental air turbine hand piece, in which a porous retainer produced by the present invention is assembled.

(i) As a nondrying oil other than the above-described olive oil, there is arachis oil.

Arachis oil is found at a content of 40–50% in seeds of *Arachis hypogaea*, and is derived from its seeds by pressing.

(ii) As a nondrying oil other than the above-described olive oil, there is oleysol oil.

Oleysol oil is available from a mutant species of sunflower, which has a high content of linoleic acid (poly-unsaturated) which is not a nondrying oil. Owing to the efforts of agricultural chemical engineers to date, it has been succeeded in growing a sunflower of mutant species which abundantly contains oleic acid (mono-unsaturated fatty acid). From this mutant species, oil named "Oleysol" is produced. Oleysol oil is a nondrying oil similar to the above-described olive oil.

Differences between the above-described nondrying vegetable oils, which can make up lubricating oils, and some semidrying vegetable oils and other edible oils are shown below in Table 1. In Table 1, olive oil, arachis oil and oleysol oil are nondrying vegetable oils considered to be preferred as lubricating oils, while the remaining oils indicate semidrying vegetable oils and drying oils as controls for the above-described nondrying vegetable oils.

In Table 1, the notes have the following meanings:

(1) composed primarily of oleic acid, and containing palmitoleic acid,
(2) linoleic acid,
(3) linolenic acid, and
(4) composed of palmitic acid, stearic acid, lauric acid and myristic acid.

In Table 1, asterisk (*) indicates control vegetable oils.

TABLE 1

Comparison between Nondrying Vegetable Oils and Other Edible Oils

| | Average constituent fatty acids (%) | | | | | Ratio of vitamin E/ poly-unsaturated fatty acids (mg/g) |
|---|---|---|---|---|---|---|
| | Unsaturated fatty acids | | | Saturated fatty acids (4) | Vitamin E (mg/kg) | |
| | Mono- (1) | Di- (2) | Tri- (3) | | | |
| Olive oil | 70 | 12 | 0.5–1.5 | 15 | 150 | 1.11 |
| Arachis oil | 60 | 25 | — | 15 | 150 | 0.60 |
| Oleysol oil | 80 | 10 | | 10 | | |
| rapeseed oil* | 60 | 22 | 10 | 8 | 150 | 0.47 |
| Sunflower oil* | 20 | 70 | 10 | 10 | 250 | 0.315 |
| Soybean oil* | 23 | 55 | 7 | 15 | 175 | 0.28 |
| Corn oil* | 26 | 60 | 2 | 12 | 200 | 0.32 |
| Coconut oil* (solid fat) | 8 | 2 | <1 | 90 | | |

From Table 1, the following tendencies are apparent.

(i) A nondrying vegetable oil contains oxidation-resistant mono-unsaturated fatty acids in a large total amount.

(ii) A nondrying vegetable oil contains oxidation-susceptible di- to tri-unsaturated fatty acids, namely, poly-unsaturated fatty acids in a small total amount.

(iii) A nondrying vegetable oil contains tocopherols (vitamin E and the like) having anti-oxidation effects at a high ratio relative to poly-unsaturated fatty acids.

In nondrying vegetable oils (olive oil, arachis oil, oleysol oil, and the like) which can make up lubricating oils for rolling bearings according to the present invention in high-speed rotating equipments such as dental air turbine hand pieces, lubrication characteristics become better as the total content of free fatty acids (saturated and unsaturated) becomes lower.

These tendencies were found in the course of the present inventors' investigation toward improvements in the lubricating characteristics of nondrying vegetable oils and, as will be explained subsequently herein, are supported by substantiating data.

Concerning the above-mentioned fatty acids (which may hereinafter be called "free fatty acids") liberated into a nondrying vegetable oil, a description will hereinafter be made.

In general, an oil or fat (a fat such as beef tallow, lard or butter; or a fatty oil such as rapeseed oil, tung oil or linseed oil) is composed of glycerol esters of higher fatty acids.

Namely, in a nondrying vegetable oil useful for a porous retainer produced in accordance with the production process of the present invention, various fatty acids (saturated and unsaturated) exist as esters represented by the following formula (1):

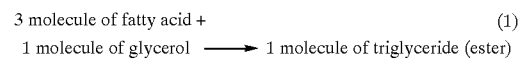

3 molecule of fatty acid + (1)
1 molecule of glycerol ⟶ 1 molecule of triglyceride (ester)

However, the nondrying vegetable oil also contains various fatty acids (free fatty acids) which are not combined with glycerol ($CH_2OH$—$CHOH$—$CH_2OH$). Expressing the total content of the above-mentioned free fatty acids in terms of free acid value, the lower this value, the lower the acidity and the more shifted toward a higher viscosity side the viscosity. A non-drying vegetable oil having a lower free acid value is therefore excellent in durability as a lubricating oil for a rolling bearing.

Based on the above-described free acid value, olive oil is classified in quality as shown below in Table 2. As will be apparent from Table 2, olive oil of higher quality has a lower free acid value and, as will be described subsequently herein, shows better lubricating characteristics (see Table 3).

To lower the free acid value of a nondrying vegetable oil such as olive oil, a method to be described next can be adopted by way of example. Namely, when olive oil is heated subsequent to addition of a 5–10% aqueous solution of sodium hydroxide, the olive oil is saponified to form glycerol and the sodium salts of fatty acids. The resulting glycerol esterifies free fatty acids. Subsequent removal of oils and fats by centrifugation can provide olive oil having a low free acid value.

In Table 2, the names of various grades of olive oil are trade names of olive oils produced by Golden Eagle Olive Products, U.S.A.

TABLE 2

Free Acid Values of Olive Oil

| Grade of olive oil | Free acid value (wt. %) |
|---|---|
| Refined oil | 0.1 |
| Extra virgin oil | 1.1 |
| Virgin oil | 3.2 |

As lubricating oils for a rolling bearing in a high-speed rotating equipment such as a dental air turbine hand piece, said rolling bearing having a porous retainer produced by the present invention, a variety of conventionally-known base oil components of the mineral oil base (natural type) or the synthetic type can also be used in addition to the above-described nondrying vegetable oils.

Illustrative of the base oil components of this type, namely, of the mineral oil base (natural type) or the synthetic type are mineral oils (paraffin oils), olefin oligomers, phosphate esters, organic acid esters, silicone oils, polyalkylene glycols, and fluorinated oils.

Compared with the above-described nondrying vegerable oils, these base oil components are inferior in biosafety and environmental conservation. Nonetheless, they are still sufficiently usable depending on the application field of the equipment.

The present invention will hereinafter be described in further detail on the basis of the following example.

In the subsequent description, each porous retainer according the present invention will be called "dissolved-out porous" because it was rendered porous by solvent dissolution, while each porous retainer rendered porous by conventional sintering will be referred to as "sintered porous".

(1) Production examples of dissolved-out porous PAI retainers:

(i) Example in which the step (2) of the present invention was performed by compression molding:

A PAI resin powder ("Torlon 4000 TF", trade name; product of Teijin-Amoco Engineering Plastics, Ltd.) and a polyether imide (PEI) resin powder ("Ultem 1000", trade name; product of General Electric Company) were each classified and sifted to have a particle size distribution of 20.4 $\mu$m in average particle size. Eighty parts by weight of the PAI resin powder and 20 parts by weight of the PEI resin powder were blended. Subsequent to thorough mixing in a Henschel mixer, the resulting blend was compression molded at a premolding pressure of 3,000 kg/cm$^2$ and a heating temperature of 300° C., whereby a non-porous retainer was obtained.

The non-porous retainer was immersed in a methylene chloride solution, to which ultrasonic waves were applied at 25° C. for 30 minutes on an ultrasonic washer to dissolve out the PEI resin so that the non-porous retainer was rendered porous in its entirety. As a result, its porosity was 17%.

(ii) Example in which the step (2) of the present invention was performed by injection molding:

Sixty-five parts by weight of a PAI resin powder ("Torlon 4000 T", trade name; product of Teijin-Amoco Engineering Plastics, Ltd.) and 35 parts by weight the polyether imide (PEI) resin powder ("Ultem 1000", trade name; product of General Electric Company) were blended. Subsequent to thorough mixing in a Henschel mixer, the resulting blend was extruded and pelletized into pellets through a twin-screw melt extruder. The pellets were charged in an injection molding machine and were then injection molded into a given mold, whereby a non-porous retainer was molded.

The non-porous retainer was next immersed in a methylene chloride solution, to which ultrasonic waves were applied at 25° C. for 30 minutes on the ultrasonic washer to dissolve out the PEI resin so that the non-porous retainer was rendered porous around its surface layer. As a result, only the surface layer and its vicinity portion were rendered porous and as a whole, the resultant porous retainer had a porosity of 2%.

Figure 3:
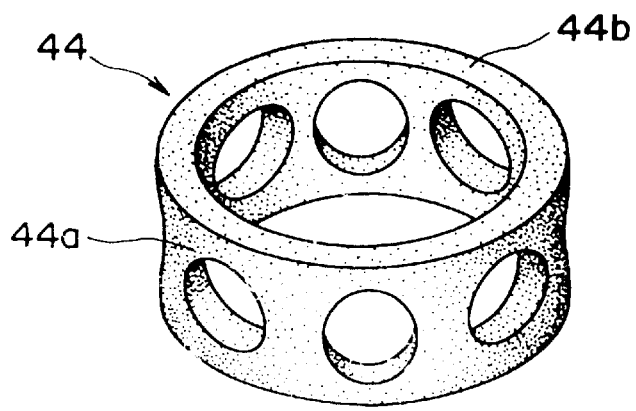
FIG. 3 is a perspective view of a retainer according to a first embodiment of the present invention shown in FIG. 2, in which the retainer is composed of a molded dissolved-out porous body.

FIG. 3 is a perspective view of a retainer 44 composed of the above-mentioned dissolved-out porous PAI resin. In the figure, symbol 44a indicates a retainer main part, and symbol 44b designates pores.

Incidentally, the retainer 44 is applied to the dental air turbine hand piece of the ball bearing type described with reference to FIG. 1 to FIG. 2.

In the present invention, the shape and structure of the retainer 44 shall not be limited to those illustated in FIG. 3.

Figure 4:
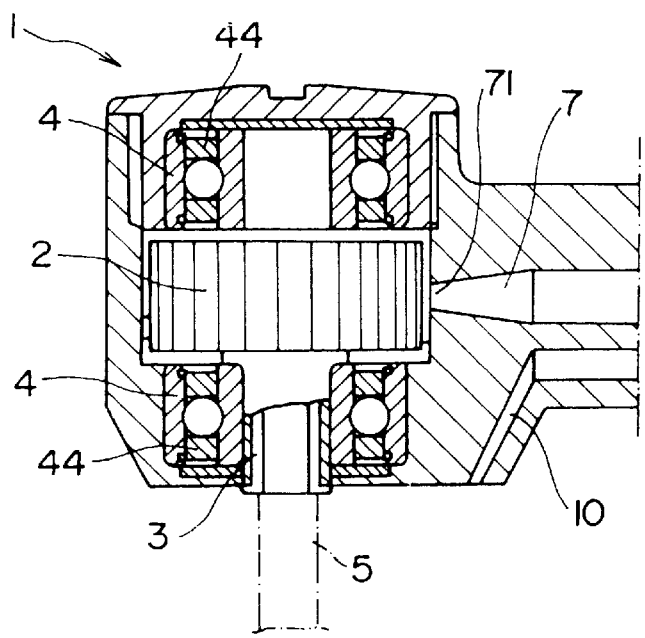
FIG. 4 is a cross-sectional view similar to FIG. 2, but illustrates another dental air turbine hand piece equipped with a retainer according to a second embodiment of the present invention, in which the retainer is composed of a molded dissolved-out porous body.
Figure 5:
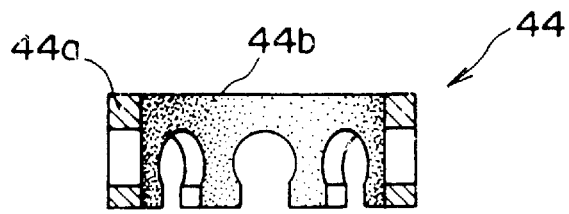
FIG. 5 is a cross-sectional view of the retainer depicted in FIG. 4.

FIG. 4 to FIG. 5 illustrate another embodiment of the retainer 44 composed of the molded dissolved-out porous PAI resin body.

Figure 2:
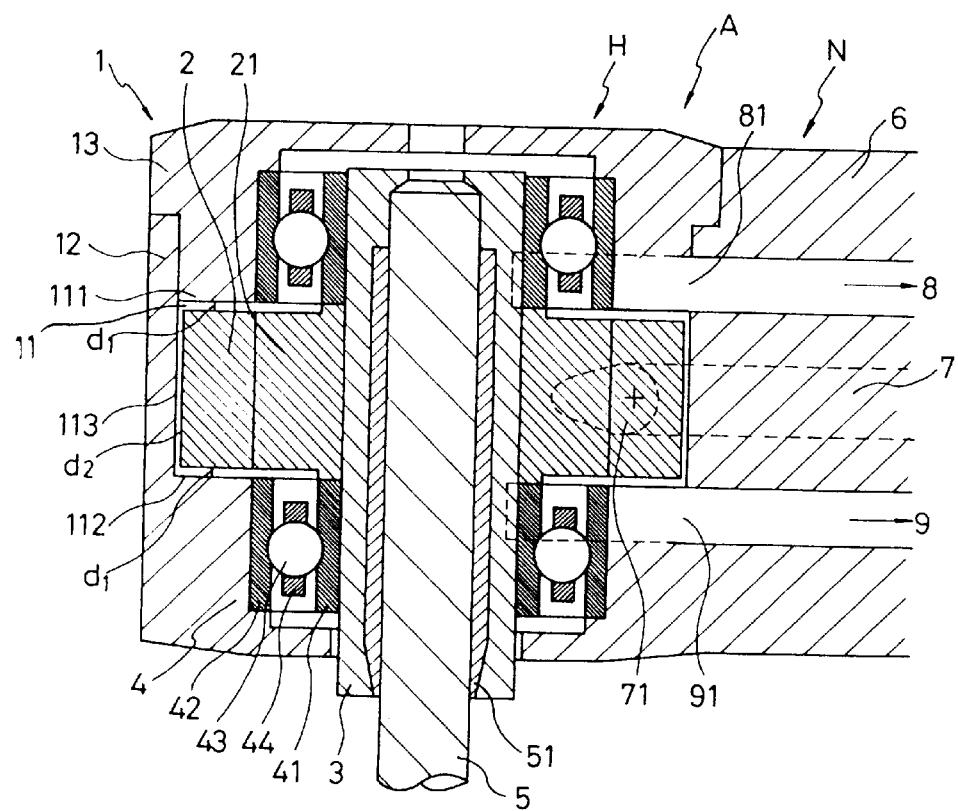
FIG. 2 is a cross-sectional view of a head portion and a neck portion of the dental air turbine hand piece of FIG. 1.

Specifically, FIG. 4 illustrates a dental air turbine hand piece in which the retainer 44 is of a structure different from that shown in FIG. 2. A description of the structure of the dental air turbine hand piece in FIG. 4 is omitted herein, because it is clear from the above-described corresponding FIG. 2.

On the other hand, FIG. 5 illustrates the shape and structure of the retainer 44 and corresponds to the above-described FIG. 3. In FIG. 5, symbol 44a indicates a main retainer part while symbol 44b designates pores.

(2) Evaluation of characteristics of dissolved-out porous PAI retainers:

The results of an evaluation of characteristics in lubrication systems of dental air turbine hand pieces in which various lubricating oils were used are shown below in Table 3.

Rolling bearings of the dental air hand pieces (see FIG. 1 to FIG. 2) furnished for use in the test of this example had the following construction:

Miniature rolling bearings of the open type, each of which was provided with a snap retainer and had the following dimensions:
(i) Inner diameter of an outer ring: 6.350 mm
(ii) Inner diameter of an inner ring: 3.175 mm
(iii) Width: 2.380 mm The above bearings was assembled in the dental air turbine hand pieces, and the test was conducted under the following conditions: air supply pressure, 2.4 kg/cm$^2$; air supply rate, 26 l/min; revolution speed, about 400,000 rpm.

(3) Production examples of dissolved-out porous PI retainers:

(i) Example in which the step (2) of the present invention was performed by compression molding:

A PI resin powder ("Meldin 2000", trade name; product of Furon) and the polyether imide (PEI) resin powder ("Ultem 1000", trade name; product of General Electric Company) were each classified and sifted to have a particle size distribution of 20.4 $\mu$m in average particle size. Eighty parts by weight of the PI resin powder and 20 parts by weight of the PEI resin powder were blended. Subsequent to thorough mixing in a Henschel mixer, the resulting blend was compression molded at a premolding pressure of 1,000 kg/cm$^2$ and a heating temperature of 390° C., whereby a non-porous retainer was obtained.

The non-porous retainer was immersed in a methylene chloride solution, to which ultrasonic waves were applied at 25° C. for 30 minutes on the ultrasonic washer to dissolve out the PEI resin so that the non-porous retainer was rendered porous in its entirety. As a result, its porosity was 5%.

(ii) Example in which the step (2) of the present invention was performed by injection molding:

Sixty-five parts by weight of a PI resin powder ("Aurum 450", trade name; product of Mitsui-Toatsu Chemicals Inc.) and 35 parts by weight the polyether imide (PEI) resin powder ("Ultem 1000", trade name; product of General Electric Company) were blended. Subsequent to thorough mixing in a Henschel mixer, the resulting blend was extruded and pelletized into pellets through a twin-screw melt extruder. The pellets were charged in the injection molding machine and were then injection molded into the given mold, whereby a non-porous retainer was molded.

The non-porous retainer was next immersed in a methylene chloride solution, to which ultrasonic waves were applied at 25° C. for 30 minutes on the ultrasonic washer to dissolve out the PEI resin so that the non-porous retainer was rendered porous around its surface layer. As a result, only the surface layer and its vicinity portion were rendered porous and as a whole, the resultant porous retainer had a porosity of 2%.

(4) Evaluation of characteristics of dissolved-out porous PI retainers:

Characteristics evaluated in lubrication systems of dental air turbine hand pieces in which various lubricating oils were used are shown below in Table 3.

In Table 3, the notes have the following meanings:

(1) <Heat resistance test (autoclaving resistance; cycles)>

An autoclaving apparatus ("ALPHI", trade name; manufactured by J. MORITA MFG. CORP.) was used. Autoclaving resistance is expressed in terms of cycles until the rotation of the dental air turbine hand piece became unstable and the efficiency of rotation dropped to 10% (about 40,000 rpm).

Conditions for the treatment in the autoclaving apparatus "ALPHI" were: steam pressure, 2.4 kg/cm$^2$; temperature, 135° C.; time, 5 minutes.

The non-porous PI·R was obtained by forming "Vespel SP-1" (trade name, product of E.I. du Pont de Nemours & Co., Ltd.) into a retainer-like shape. On the other hand, the non-porous PAI·R was obtained by forming "Torlon 4203"(trade name, product of Teijin-Amoco Engineering Plastics, Ltd.) into a retainer-like shape.

(ii) Sintered porous PI/PAI·R:

The sintered porous PI·R was obtained by compression-molding "UIP-S" (trade name, product of Ube Industries, Ltd.) under a molding pressure of 4,000 kgf/cm$^2$, sintering the green compact at 400° C. in a nitrogen gas atmosphere and then machining the sintered compact into a retainer-like shape (porosity: about 13% by volume).

The sintered porous PAI·R was obtained by classifying and sifting "Torlon 4000TF" (trade name, product of Amoco Chemical Corp., U.S.A.) into an average particle size of 20 μm, compression-molding the thus-shifted powder under a preforming pressure of 2,800 kgf/cm$^2$, sintering the green compact at 300° C., and then machining the sintered compact into a retainer-like shape (porosity: about 14% by volume).

In Table 3, the following products were used as the paraffin oil and the fluorinated oil.

(a) As the paraffin oil (liquid paraffin), a conventional spray-type paraffin oil produced by an odontotherapy-related maker was used.

(b) As the fluorinated oil, "FOMBLIN" (trade name, product of Ausimont S.p.A., Italy) was used.

TABLE 3

Evaluation of Characteristics of Various Lubricating Oils

| Lubricating oil | | | Bio-safety | Environmental conservation | Heat resistance (1) (autoclaving resistance, cycles) | | | Bearing resistance (2) (continuous rotation, hrs) | | |
|---|---|---|---|---|---|---|---|---|---|---|
| | | | | | (i) Non-porous PI/PAI·R | (ii) Sintered porous PI/PAI·R | (iii) Dissolved-out porous PI/PAI·R | (i) Non-porous PI/PAI·R | (ii) Sintered Porous PI/PAI·R | (iii) Dissolved-out porous PI/PAI·R |
| Vegetable oil | Nondrying oil | Refined olive oil | A | B | 1000< | 1000< | 1000< | 1.50 | 29.75 | 29.00 |
| | | Extra virgin olive oil | A | B | 1000< | 1000< | 1000< | 2.00 | 25.50 | 23.00 |
| | | Virgin olive oil | A | B | 1000< | 1000< | 1000< | 1.75 | 18.25 | 17.00 |
| | | Arachis oil | A | B | 1000< | 1000< | 1000< | 1.50 | 18.50 | 18.50 |
| | Semidrying oil | Rapeseed oil | A | B | 300 | 300 | 300 | 0.25 | 4.50 | 4.00 |
| Mineral oil | Paraffin oil | | C | C | 1000< | 200 | 1000< | 0.50 | 8.50 | 7.00 |
| Synthetic oil | Fluorinated oil | | C | C | 1000< | 1000< | 1000< | 1.50 | 17.50 | 18.00 |

A: Excellent, B: Good, C: Poor (2) <Bearing resistance (continuous operation; hrs)>

Each lubricating oil was applied to a lubrication system of the dental air hand piece at the beginning, and a continuous operation was then performed at about 400,000 rpm without additional feeding of the lubricating oil. The bearing resistance is expressed in term of hours until the rotation become unstable and the revolution speed dropped to 10% (about 40,000 rpm).

The retainers shown as comparative examples in Table 3, namely, the non-porous PI/PAI·R and the sintered porous PI/PAI·R have the following meanings:

(i) Non-porous PI/PAI·R:

As is shown in Table 3, it is understood that the dissolved-out porous PI/PAI retainers (PI/PAI·R) according to the production process of this invention have characteristics far superior to the non-porous PI/PAI retainers (PI/PAI·R) according to the conventional production process. Even when compared with the conventional sintered porous PI/PAI retainers (PA/PAI·R), they are understood to be comparable.

In the evaluation of the superiority of the dissolved-out porous PI/PAI retainers (PI/PAI·R) according to the present invention to the conventional sintered porous PI/PAI retainers (PI/PAI·R), it should not be overlooked that the production process according to the present invention is simpler and easier for practice and is more economical than the conventional process.

We claim:

1. A process for the production of a porous retainer for use in a rolling bearing for holding rolling elements, which comprises the following steps:

(1) blending a powdered polyimide resin, which serves as a porous matrix material for said porous retainer, with another heat-resistant powdered resin which has a forming temperature range close to said polyimide resin and, when treated with a solvent in tie presence of said polyimide resin, is solely dissolved out;

(2) forming the resulting resin blend into a shape of a retainer for holding rolling elements in a rolling bearing; and (3) treating the thus-formed retainer with said solvent, thereby solely dissolving said another heat-resistant resin out of said retainer.

2. The process according to claim 1, wherein said another heat-resistant resin is at least one resin selected from the group consisting of polyether sulfones (PESs), polyether imides (PEIs), polyarylates (PARs) and polysulfones (PSFs).

3. The process according to claim 1, wherein said solvent is methylene chloride (dichloromethane).

4. The process according to claim 1, wherein during blending said polyimide resin and said another heat-resistant resins are each in a form of powder having an average particle size of from 15 to 50 μm.

5. The process according to claim 1, wherein said porous retainer obtained in the solvent dissolution step (3) has a porosity of from 0.5 to 20% by volume.

* * * * *